United States Patent [19]

Kono et al.

[11] Patent Number: 4,970,069
[45] Date of Patent: Nov. 13, 1990

[54] METHOD OF ATTRACTING *TRIBOLIUM CASTANEUM HERBST* WITH 2,6-DIMETHYL-OCTLY FORMATE

[75] Inventors: Masahiro Kono; Tatsuji Chuman; Takane Fujimori, all of Yokohama; Kenji Mori, Tokyo; Shigefumi Kuwahara, Matsudo, all of Japan

[73] Assignee: Japan Tobacco, Inc., Tokyo, Japan

[21] Appl. No.: 172,705

[22] Filed: Mar. 23, 1989

[30] Foreign Application Priority Data

Mar. 23, 1987 [JP] Japan ................................. 62-65660

[51] Int. Cl.$^5$ ........................................ A01N 37/02
[52] U.S. Cl. ...................................... 424/84; 560/265
[58] Field of Search ........................... 560/265; 424/84

[56] References Cited

PUBLICATIONS

Kuwahara, Y., Chemical Abstracts, 96:159689k, 1982.
Givaudan, L., Chemical Abstracts, vol. 72:42806j, 1970.
Suzuki, Takahisa, "4,8-Dimethyl-Decanal: The Aggregation Pheromone of the Flour Beetles, *Tribolium castaneum* and *T. Confusum* (Coleoptera: Tenebrionidae)", p. 220, column 1, abstract no. 13037h.
Chemcial Abstracts, vol. 94, No. 3, Jan. 19, 1981, Suzuki Takahisa, Agric. Biol. Chem., 1980, 44(10), 2519–20.
O. K. Jacobi, "Cosmetics and Detergents Additives to Reduce Skin Irritation and Skin Fat Removal", p. 212, column 1, Abstract No. 4891v, Chemical Abstracts, vol. 73, No. 10, Sep. 7, 1970.

*Primary Examiner*—Vivian Garner
*Attorney, Agent, or Firm*—McGlew and Tuttle

[57] ABSTRACT

According to the present invention, an attractant that possesses attraction effects with respect to *Tribolium castaneum* Herbst and moreover, is a stable compound for which the effectiveness will be continuous, is provided.

That is, the present invention is 2,6-dimethyl octylformate and an atrractant of *Tribolium castaneum* Herbst which is formed from relevant chemical compounds.

4 Claims, No Drawings

METHOD OF ATTRACTING *TRIBOLIUM CASTANEUM HERBST* WITH 2,6-DIMETHYL-OCTLY FORMATE

DESCRIPTION

1. Technical Field

This invention relates to 2,6-dimethyl octylformate and an attractant of *Tribolium castaneum* Herbst (Rust-red flour beetle) which is formed from relevant chemical compounds.

2. Background Art

*Tribolium castaneum* Herbst is the most ubiquitous beetle species that is harmful to grains and cereals. It is a major indoor harmful insect that attacks not only grains such as wheat flour, but also secondary processed grain products such as cakes and breads, medicinal herbs, spices and animal specimens.

In the case of indoor harmful insects such as this, as there is a high degree of involvement with people, there are restrictions in terms of safety and health when taking eradication measures. There are numerous cases when effective eradication measures used for other harmful insects cannot be implemented. For example, in specified warehouses, although highly toxic fumigants such as hydrogen phosphide and methyl bromide are being used, in factory warehouses and workshops where there is a high volume of worker traffic, there are greater health and sanitation standards, resulting in only the use of extremely minute amounts of DDVP being allowed. However, because DDVP has no residual effectiveness or penetration properties, even if it is able to kill adult insects existing in areas that can easily come in contact with the drug, with respect to adults, eggs, larvae and pupae that exist hiding in corners and other concealed areas of the factory, it is essentially ineffective. Therefore, it is necessary to apply the drug frequently. However, the problem with this is that even if the concentration of living adults is decreased temporarily, with the emergence of wings on the developing immature insects, the concentration of living adults is restored to its previous level in a short period of time.

On the other hand, research has recently been progressing rapidly on chemicals and technology relating to eradication methods such as eradication by attracting and killing harmful insects and eradication by disturbing communication between males and females using sex pheromones of insects. In general, insect mating behavior is controlled by minute amounts of aromatic substances secreted by the insect itself (most commonly by the female). Male adults sense the volatile aromatic substances produced by the female adults, approach the female adults either by flying or crawling, elicit sexual excitation which leads to mating. The above aromatic substance is generally referred to as sex pheromone. In contrast to this, there is a pheromone that is secreted from male adults which is used for communication between not only males and females but also between fellow males simultaneously attracting both male and female adults. This is referred to as aggregation pheromone. The secretion produced by *Tribolium castaneum* Herbst belongs to this category.

It is possible to implement eradication of harmful insects utilizing sex pheromones and aggregation pheromones by catching and killing after attracting both male and female adults to a specific location, or by destroying the ecosystem by artificially disturbing normal mating behavior. In addition, it is possible to perceive beforehand the state of proliferation of harmful insects that are the potential targets of eradication using these same pheromones.

We studied the development of an attractant using 4,8-dimethyl decanal [Suzuki, Agric. Biol. Chem., 44 (10), 2519–2520, 1980] which is the aggregation pheromone of *Tribolium castaneum* Herbst. Since this substance is an aldehyde compound, it is easily oxidized. As a result, since it rapidly loses its attraction activity, it has problems in terms of practical use. Therefore, we attempted research and development of a new substance that possesses attraction activity that can be used in place of the above-mentioned aggregation pheromone. The purpose of this invention is to provide an attractant that possesses attraction effects with respect to *Tribolium castaneum* Herbst and moreover, is a stable compound for which the effectiveness will be continuous.

DISCLOSURE OF THE INVENTION

We synthesized numerous compounds possessing a chemical structure resembling the pheromone of *Tribolium castaneum* Herbst described above. As a result of testing for the presence or absence of attraction effects of these with respect to *Tribolium castaneum* Herbst, we found that the compound having the structural formula shown below, that is, 2,6-dimethyl octylformate, exhibits extremely powerful attraction effects on adult *Tribolium castaneum* Herbst, whereby the present invention is attained.

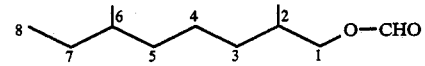

In other words, this invention is the compound having the structure as above and an attractant of *Tribolium castaneum* Herbst comprising said compound as an effective ingredient.

It is possible to produce 2,6-dimethyl octylformate from methyl malonic acid dimethyl ester [hereinafter referred to as Compound (1)] via the 5-step synthesis route indicated in a–e below.

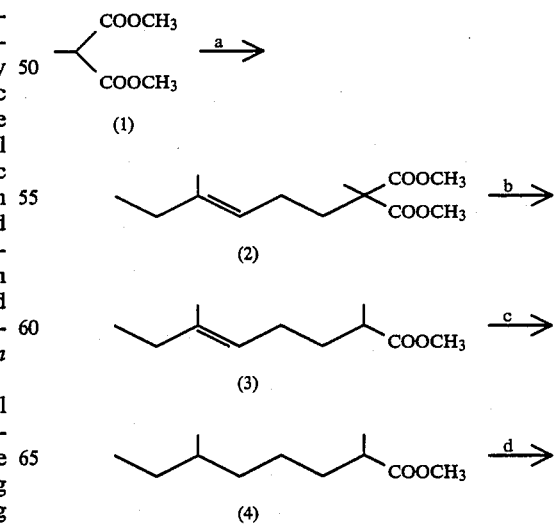

-continued (5) [structure: branched chain with OH] →e→

(compound of this invention) [structure: branched chain with O—CHO]

BEST MODES FOR CARRYING OUT THE INVENTION

The preparation process of the compound of this invention will be described in sequence following the each of the synthesis routes indicated above.

a. In the presence of sodium hydride, 4-methyl-3-hexenyl bromide was reacted with Compound (1) to obtain dimethyl (4-methyl-3-hexenyl-methyl malonic acid dimethyl ester [hereinafter referred to as Compound (2)]. In this reaction, a proportion of 0.5–2 moles of 4-methyl-3-hexenyl bromide was used for 1 mole of Compound (1). The reaction was carried out for 6 to 12 hours at a reaction temperature of 0°–100° C.

b. Compound (2) was reacted with sodium chloride in dimethyl sulfoxide to obtain 2,6-dimethyl-5-octenoic acid methyl ester [hereinafter referred to as Compound (3)]. In this reaction, a proportion of 1.5–3 moles of sodium chloride was used for 1 mole of Compound (2) and the reactants were refluxed for 15–30 hours.

c. Compound (3) was reacted with hydrogen gas in methanol with 10% palladium carbon as a catalyst to obtain 2,6-dimethyl-5-octonoic acid methyl ester [hereinafter referred to as Compound (4)]. 30–50 g of the catalyst was used per 1 mole of Compound (3). The reaction was carried out at a temperature of 15°–20° C. at atmospheric pressure.

d. Compound (4) was reacted with lithium aluminum hydride in anhydrous ether to obtain 2,6-dimethyl-1-octanol [hereinafter referred to as Compound (5)]. 1–2 moles of lithium aluminum hydride were used per 1 mole of Compound (4) and were reacted for 1–3 hours at a temperature of −10°–0° C.

e. Compound (5) was reacted with formic acid to obtain 2,6-dimethyl octylformate, the compound of this invention. In this reaction, formic acid was used in the proportion of 1–2 liter per 1 mole of Compound (5) and the reactants were reacted at a temperature of 60°–80° C. for 20–60 minutes.

The compound of this invention obtained in this way can be used as an attractant of *Tribolium castaneum Herbst*. With respect to its method of use, although the compound of this invention may be used as is placing it inside of a trap, it is most commonly used in plastic capsule or in tablet form contained in a suitable carrier. As a carrier, synthetic resin, sand, diatom earth, silica gel or the like is used suitably. For example, mixing the compound in a proportion of about 1–30 mg for each gram of carrier composed of polypropylene powder and pulp and then forming into tablets yields satisfactory results.

As is clear from the examples to follow, the compound of this invention possesses excellent effectiveness as an attractant of *Tribolium castaneum Herbst*. Therefore, by using the compound of this invention, it is possible to eradicate adult *Tribolium castaneum Herbst* by either catching and killing them after attracting them to a specific location or disturbing the normal ecosystem between adults. In addition, by investigating the proliferation of *Tribolium castaneum Herbst* using this attractant, it is possible to take effective preventative measures such as being able to determine its appropriate time of use along with the suitability of its use with other insecticides.

The following examples are given to further illustrate the present invention, but not by way of limitation.

EXAMPLE 1: PRODUCTION EXAMPLE

Synthesis of 2,6-dimethyl octylformate 3.5 g of 60% sodium hydride (8.75 millimoles) was washed three times using 5 ml of n-pentane in an argon atmosphere. A solution of 13 g of Compound (1) (8.9 millimoles) in 30 ml of anhydrous tetrahydrofuran was dropped into this while water-cooling at 10° C. This was then stirred for 10 minutes at room temperature. A solution of 13 g of 4-methyl-3-hexenyl bromide (7.34 millimoles) in 13 ml of anhydrous tetrahydrofuran was dropped into this at room temperature. This was stirred overnight at room temperature following 8 hours of refluxing after dropping was completed. The reaction solution which had been thus obtained was poured into a saturated aqueous solution of ammonium chloride followed by extraction with ether. The ether layer was taken off and then sequentially washed with water and a saturated aqueous solution of sodium chloride. This was followed by filtration after drying with anhydrous magnesium sulfate. The filtrate was concentrated under reduced pressure to remove the ether whereby 19.72 g of raw Compound (2) was obtained.

The physicochemical properties of this Compound (2) are:

Infrared Absorption Spectrum (cm$^{-1}$):
1735(s), 1260(s), 1235(s), 1160(s), 1110(s), 870(m).

Next, 19.72 g of the raw Compound (2) was dissolved in 55 ml of dimethyl sulfoxide followed by the addition of 3.2 ml of water and 5.9 g of sodium chloride. This solution was then refluxed for 20 hours. The reaction solution was poured into water followed by extraction of the reaction products with ether. The ether layer was sequentially washed with water and a saturated aqueous sodium chloride solution and after drying with anhydrous magnesium sulfate, the solution was concentrated under reduced pressure to remove the ether whereby 13.7 g of raw Compound (3) was obtained. This was then purified using silica gel column chromatography followed by distillation under reduced pressure to obtain 9.72 g of Compound (3).

The physicochemical properties of Compound (3) are:

Boiling Point: 110°–111° C. (25 mmHg).
Molecular Formula: $C_{11}H_{20}O_2$.
Infrared Absorption Spectrum (cm$^{-1}$):
1740(vs), 1200(s), 1160(s), 845(m).
Nuclear Magnetic Resonance Spectrum:
0.96(3H,t,J=7Hz), 1.11(3H,d,J=7Hz), 1.56(3H,s), 1.2–2.6(7H,m), 3.60(3H,s), 5.03(1H,t,J=7Hz).

Next, 5.0 g of the above Compound (3) (2.72 millimoles) was dissolved in 50 ml of methanol. 0.7 g of 10% polladium-carbon was added as a catalyst. This solution was then shaken at room temperature in a hydrogen atmosphere at atmospheric pressure. After filtering to separate the catalyst, the filtrate was concentrated under reduced pressure followed by distillation under reduced pressure to obtain 4.70 g of Compound (4).

The physicochemical properties of Compound (4) are:
  Boiling Point: 114°–116° C. (35 mmHg).
  Molecular Formula: $C_{11}H_{22}O_2$.
  Infrared Absorption Spectrum(cm$^{-1}$): 1740(s), 1200(m), 1170(s).
  Nuclear Magnetic Resonance Spectrum:
  0.7–1.0(6H,m), 1.09(2H,d,J=7Hz), 1.1–1.9(9H,m), 2.1–2.6(1H,m), 3.59(3H,s).

Next, a solution of 4.0 g of the above Compound (4) (2.15 millimoles) in 10 ml of anhydrous ether was dropped into a suspension of 0.85 g of lithium aluminum hydride (2.24 millimoles) in 10 ml of anhydrous ether while water-cooling at −5°–0° C. After stirring for 1 hour, 0.85 ml of water, 0.85 ml of a 15% solution of aqueous sodium hydroxide and 2.55 ml of water were added sequentially followed by stirring for 30 minutes. After filtering and separation of the crystals that formed, the filtrate was concentrated under reduced pressure followed by distillation under reduced pressure to obtain 3.24 g of Compound (5).

The physicochemical properties of Compound (5) are:
  Boiling Point: 117°–119° C. (26 mmHg).
  Molecular Formula: $C_{10}H_{22}O$.
  Infrared Absorption Spectrum (cm$^{-1}$): 3350(s), 1040(s).
  Nuclear Magnetic Resonance Spectrum:
  0.7–1.0(9H,m), 1.0–1.9(10H,m), 3.26(2H,d,J=6Hz), 3.11(1H,s).

Next, 0.856 g of the above Compound (5) (4.6 millimoles) was dissolved in 10 ml of 98% purity formic acid. This solution was stirred for 30 minutes at a temperature of 65°–70° C. The reaction solution was poured a little at a time into a saturated aqueous solution of sodium hydrogencarbonate and ice and then extracted with ether. The ether layer was sequentially washed with a saturated aqueous solution of sodium hydrogencarbonate and a saturated solution of sodium chloride. Following drying with anhydrous magnesium sulfate and filtration, the filtrate was concentrated under reduced pressure to obtain 1.0 g of the raw form of the compound of this invention. After purification with silica gel chromatography, distillation under reduced pressure was performed on the purified product to obtain 0.817 g of the compound of this invention.

The physicochemical properties of the compound of this invention are:
  Boiling Point: 109°–111° C. (23 mmHg).
  Molecular Formula: $C_{11}H_{22}O_2$.
  Infrared Absorption Spectrum (cm$^{-1}$): 1730(s), 1180(s).
  Nuclear Magnetic Resonance Spectrum:
  0.89(3H,t,J=6Hz), 0.94(3Hx2,d,J=6Hz), 1.0–2.1(10H,m), 3.92(2H,d,J=6Hz), 7.99(1H,s).

EXAMPLE 2

2 pieces each of circular filter paper 21 mm in diameter were placed in 5 plastic laboratory dishes 85 mm in diameter such that the pieces of filter paper were separated by a space of 30 mm. One of the pieces of filter paper was impregnated with the 5 test solution standards indicated in Table 1 and the other was made to serve as the control by impregnating with solvent only. Acetone was used for the solvent. After volatilizing the solvent, 30 Tribolium castaneum Herbst adult beetles were placed in each of the laboratory dishes. Each of the dishes was covered and the attraction to the filter paper was investigated. The experiment was repeated 6 times indoors at a temperature of 28° C. under red light. Effectiveness was accessed by examining the average value of the number of beetles that gathered on each of the pieces of filter paper at a point 5 minutes after the beetles had been placed in the laboratory dishes. The results are shown in Table 1.

TABLE 1

| Test Solution (Amount of the compound of this invention contained) | Filter paper impregnated with the compound of this invention | Control filter paper |
| --- | --- | --- |
| 1 ng/pc. of filter paper | 7.2 | 5.2 |
| 10 ng/pc. of filter paper | 12.0 | 1.7 |
| 100 ng/pc. of filter paper | 15.8 | 2.5 |
| 1 μg/pc. of filter paper | 20.7 | 3.9 |
| 10 μg/pc. of filter paper | 18.6 | 2.2 |

Note:
The figures in the table represent the average value of the number of beetles that had gathered on each of the pieces of filter paper.

EXAMPLE 3

Each of the 5 test solution standards indicated in Table 2 was impregnated into 5 polypropylene disks 1 cm in diameter and 3 mm thick. In addition, the same number of disks were made to serve as controls and were impregnated with solvent only. Each of the disks was placed in the centers of 6 cm×15 cm rectangular pieces of cardboard coated with an adhesive. The respective disks were then made to serve as the test traps and control traps. Each of the traps was arranged on the floor of a closed cubic chamber measuring 5 m on each side at 2 m intervals. 100 Tribolium castaneum Herbst adult beetles were then released into the chamber. After release, the number of beetles that were captured on each of the traps over a period of 2 days at a temperature of 28° C. under red light was counted. After repeating the experiment 6 times, effectiveness was accessed by examining the average values of the number of beetles counted for each trap. The results are shown in Table 2.

TABLE 2

| Test Solutions (Amount of the compound of this invention contained) | Test Traps | Control Traps |
| --- | --- | --- |
| 10 ng/disk | 20.2 | 3.6 |
| 100 nga/disk | 28.9 | 2.5 |
| 1 μg/disk | 42.3 | 4.6 |
| 10 μg/disk | 31.6 | 2.2 |
| 100 μg/disk | 32.0 | 3.2 |

Note:
The figures in the table represent the average values of the number of beetles that were captured on each of the traps.

We claim:

1. Method of attracting Tribolium castaneum Herbst comprising placing at an attracting site an effective attractant amount of the compound having the structural formula ![structural formula showing a branched alkyl chain ending in O—CHO]

2. Method of attracting *Tribolium castaneum* Herbst comprising placing at an attracting site a composition of an effective attractant amount of a compound having the structural formula $$\text{(structure: branched alkyl chain)}-\text{O}-\text{CHO}$$

in association with a carrier.

3. Method of attracting *Tribolium castaneum* Herbst according to claim 2 wherein the composition is in tablet form.

4. Method of attracting *Tribolium castaneum* Herbst according to claim 2 wherein the composition is in capsule form.

* * * * *